United States Patent
Meyer et al.

(10) Patent No.: US 7,981,932 B2
(45) Date of Patent: Jul. 19, 2011

(54) SALTS OF ALKYL ESTERS OF SULFONATED DICARBOXYLIC ACIDS AND COMPOSITIONS CONTAINING SAME

(75) Inventors: Joachim Meyer, Hilden (DE); Thomas Koelen Van Der, Oberhausen (DE); Uwe Held, Velbert (DE); Stefan Busch, Oberhausen (DE)

(73) Assignee: Cognis IP Management GmbH, Duesseldorf (DE)

( * ) Notice: Subject to any disclaimer, the term of this patent is extended or adjusted under 35 U.S.C. 154(b) by 903 days.

(21) Appl. No.: 11/713,442

(22) Filed: Mar. 2, 2007

(65) Prior Publication Data

US 2007/0214999 A1 Sep. 20, 2007

(30) Foreign Application Priority Data

Mar. 3, 2006 (DE) .......................... 10 2006 009 971

(51) Int. Cl.
*A61K 31/255* (2006.01)
*C07C 323/00* (2006.01)

(52) U.S. Cl. ........................................ 514/550; 560/151

(58) Field of Classification Search .......................... None
See application file for complete search history.

(56) References Cited

U.S. PATENT DOCUMENTS 2,675,320 A * 4/1954 Christopher et al. ...... 106/31.66
3,737,552 A * 6/1973 Gordon et al. ................ 514/547

FOREIGN PATENT DOCUMENTS

| DE | 4325923 A1 | 2/1995 |
| DE | 10243363 A1 | 4/2004 |
| EP | 1415978 A1 | 5/2004 |

OTHER PUBLICATIONS

XP-002448893 "Electron Density Matching as a Guide to Sufactant Design" R. F. Tabor et al; Langmuir, Dec. 22, 2006; pp. 963-968.
International Search Report from EP07003721.
Breuer et al., "Sulfosuccinates for Emulsion Polymerization", Tenside Surf. Det. 40 (2003) 4, pp. 208-214.

* cited by examiner

*Primary Examiner* — Paul A Zucker
(74) *Attorney, Agent, or Firm* — Diehl Servilla LLC

(57) ABSTRACT

A salt of a mono- and/or dialkyl ester of a sulfonated dicarboxylic acid is provided, where the dicarboxylic acid contains 4 to 8 carbon atoms and the alkyl groups are derived from 2-propylheptanol. A composition including (a) one or more salt(s) of a mono- and/or dialkyl ester(s) of a sulfonated dicarboxylic acid(s), where the dicarboxylic acid contains 4 to 8 carbon atoms and the alkyl groups are derived from 2-propylheptanol; and (b) one or more organic solvents liquid at 20° C. with a boiling point above 250° C. at 1 bar is also provided.

13 Claims, No Drawings

SALTS OF ALKYL ESTERS OF SULFONATED DICARBOXYLIC ACIDS AND COMPOSITIONS CONTAINING SAME

CROSS-REFERENCE TO RELATED APPLICATIONS

This application claims priority under 35 U.S.C. §119 from German Patent Application No. 102006009971.0, filed Mar. 3, 2006, the entire disclosure of which is hereby incorporated by reference.

BACKGROUND OF THE INVENTION

1. Field of the Invention

The invention relates generally to salts of mono- and dialkyl esters of sulfonated dicarboxylic acids, and more particularly to compounds and compositions including salts of mono- and dialkyl esters of sulfonated dicarboxylic acids, wherein the dicarboxylic acids contain 4 to 8 carbon atoms and the alkyl groups are derived from 2-propylheptanol, and to the use of the salts.

2. Background Information

Salts of mono- and dialkyl esters of sulfonated dicarboxylic acids have been known for some time. They are also known as mono- and disulfosuccinates, respectively, and are used as surfactants inter alia in emulsion polymerization, as wetting agents for paints, for coating paper and paperboard and for pharmaceutical purposes (cf. for example the synoptic article by Breuer, W. and Höfer, R. in Tenside, Surfactants, Detergents, 2003, 40 (4), 208-214).

By virtue of its favorable properties, including for example the low dynamic surface tension of aqueous solutions, the sodium salt of di-2-ethylhexyl sulfosuccinate in particular is widely used. However, for production-related reasons and in consequence of ester cleavage reactions, the corresponding formulations contain free, i.e., unbound, 2-ethyl hexanol. In view of its unpleasant odor and taste, this free 2-ethylhexanol is a disadvantage for many applications, particularly in the food industry. In addition, both 2-ethylhexyl alcohol and the sodium salt of di-2-ethylhexyl sulfosuccinate are classified as water hazards (Water Hazard Class 2).

SUMMARY OF THE INVENTION

Briefly described, according to an aspect of the invention, a compound includes a salt of a mono- and/or dialkyl ester of a sulfonated dicarboxylic acid, where the dicarboxylic acid contains 4 to 8 carbon atoms and the alkyl groups are derived from 2-propylheptanol.

According to another aspect of the invention, a composition includes (a) one or more salt(s) of a mono- and/or dialkyl ester(s) of a sulfonated dicarboxylic acid(s), where the dicarboxylic acid contains 4 to 8 carbon atoms and the alkyl groups are derived from 2-propylheptanol; and (b) one or more organic solvents liquid at 20° C. with a boiling point above 250° C. at 1 bar.

DETAILED DESCRIPTION OF THE INVENTION

The problem addressed by the present invention was to provide salts of mono- and/or dialkyl esters of sulfonated dicarboxylic acids, more particularly sulfosuccinates, which would avoid the above-mentioned disadvantages of di-2-ethylhexyl sulfosuccinates (di-2EH-sulfosuccinates). More particularly, the problem addressed by the present invention was to provide sulfosuccinates which would not contain any free 2-ethylhexanol. Another problem addressed by the present invention was to provide sulfosuccinates which would be suitable as additives for paints and which would be distinguished in particular by an improvement in the water resistance of the corresponding paints in relation to di-2EH-sulfosuccinates.

The present invention relates to salts of mono- and/or dialkyl esters of sulfonated dicarboxylic acids, the dicarboxylic acids containing 4 to 8 carbon atoms and the alkyl groups being derived from 2-propylheptanol.

2-Propylheptanol

"2-Propylheptanol" in the context of the present invention is understood to be $C_5H_{11}CH(C_3H_7)CH_2OH$ where $C_5H_{11}$ can represent $n-C_5H_{11}$, $C_2H_5CH(CH_3)CH_2$ or $CH_3CH(CH_3)CH_2CH_2$. The 2-propylheptanol on which the sulfosuccinates of the present invention are based may be used in the form of each of the three species just mentioned or mixtures of these species.

2-Propylheptanol can be produced in various ways, for example from valeraldehyde by aldol condensation and subsequent hydrogenation. 2-Propylheptanol can also be produced by condensation of 1-pentanol (in the form of a mixture of the corresponding methylbutanols) in the presence of KOH at elevated temperatures on the lines of a Guerbet reaction. Finally, 2-propylheptanol can be obtained by hydroformylation of butenes and subsequent aldol condensation.

In one embodiment, the 2-propylheptanol used for the production of the sulfosuccinates according to the invention has a content of $n-C_5H_{11}CH(C_3H_7)CH_2OH$ of at least 98%. Substances of this purity are preferably produced by Guerbet reaction of 1-pentanol.

In another embodiment, the 2-propylheptanol used for the production of the sulfosuccinates according to the invention is present in the following commercially obtainable supply form of an isomer mixture of a) 70 to 99% of $n-C_5H_{11}CH(C_3H_7)CH_2OH$ and
b) 1 to 30% of a mixture of the alcohols $C_2H_5CH(CH_3)CH_2CH(C_3H_7)CH_2OH$ and $CH_3CH(CH_3)CH_2CH_2CH(C_3H_7)CH_2OH$.

The alkyl radicals $n-C_5H_{11}CH(C_3H_7)CH_2$, $C_2H_5CH(CH_3)CH_2CH(C_3H_7)CH_2$ and $CH_3CH(CH_3)CH_2CH_2CH(C_3H_7)CH_2$ derived from 2-propylheptanol are also referred to in short hereinafter as 2PH.

Salts of Mono- and/or Dialkylesters of Sulfonated Dicarboxylic Acids

The salts of mono- and/or dialkyl esters of sulfonated dicarboxylic acids according to the invention are derived from dicarboxylic acids containing 4 to 8 carbon atoms. They can be produced by methods known to the relevant expert.

Examples of suitable dicarboxylic acids are maleic acid, fumaric acid and succinic acid.

In a preferred embodiment, the compounds according to the invention are substances corresponding to formula (I):

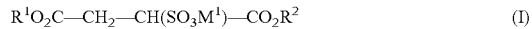

in which $M^1$ is a cation and $R^1$ and $R^2$ independently of one another have the same meaning as $M^1$ or represent an alkyl group $n-C_5H_{11}CH(C_3H_7)CH_2$, $C_2H_5CH(CH_3)CH_2CH(C_3H_7)CH_2OH$ or $CH_3CH(CH_3)CH_2CH_2CH(C_3H_7)CH_2OH$, with the proviso that at most one of the substituents $R^1$ and $R^1$ may have the meaning of $M^1$.

Particularly preferred dialkyl sulfosuccinates are compounds corresponding to formula (II):

in which $M^1$ is a cation and $R^1$ and $R^2$ independently of one another are selected from the group consisting of n-$C_5H_{11}$CH($C_3H_7$)$CH_2$, $C_2H_5$CH($CH_3$)$CH_2$CH($C_3H_7$)$CH_2$OH and $CH_3$CH($CH_3$)$CH_2$CH_2$CH($C_3H_7$)$CH_2$OH.

Preferred cations of the salts of mono- and/or dialkyl esters of sulfonated dicarboxylic acids according to the invention are the alkali metal cations sodium and potassium and the ammonium cation.

The salts of mono- and/or dialkyl esters of sulfonated dicarboxylic acids according to the invention are neutral in odor. The di-2PH-sulfosuccinate, like 2-propylheptanol, is classified as only a mild water: hazard (Water Hazard Class 1).

Mixtures

In one supply form, the salts of mono- and/or dialkyl esters of sulfonated dicarboxylic acids according to the invention are present in water. Corresponding aqueous solutions show excellent dynamic surface tension and particularly favorable foam behavior (low tendency to foam).

In order to obtain products liquid at room temperature (20° C.), co-solvents may be added if necessary to aqueous solutions of the salts of mono- and/or dialkyl esters of sulfonated dicarboxylic acids according to the invention. Examples of suitable co-solvents are ethoxylated and/or propoxylated alcohols, butyl diglycol, butyl triglycol or short-chain alcohols, such as ethanol, propanol or butanol.

The present invention relates to compositions containing
(i) one or more of the salts of mono- and/or dialkyl esters of sulfonated dicarboxylic acids according to the invention and
(ii) one or more organic solvents liquid at 20° C. with a boiling point above 250° C. at 1 bar.

The solvent (ii) is preferably a nonionic surfactant, more particularly an alcohol ethoxylate. Examples of suitable alcohols are fatty alcohols and/or oxoalcohols containing 10 to 18 and more particularly 12 to 15 carbon atoms. The degree of ethoxylation is preferably 3 to 20 and more particularly 5 to 15.

The composition may contain other constituents besides the above-mentioned components (i) and (ii), more particularly short-chain alcohols and/or water as a diluent or auxiliary solvent.

Uses

The substances according to the invention and the aqueous solutions and above-mentioned mixtures thereof may be used as emulsifiers and/or dispersants for a variety of applications.

The present invention also relates to the use of the substances according to the invention and the aqueous solutions and above-mentioned mixtures thereof as emulsifiers for emulsion polymerization.

The present invention also relates to the use of the substances according to the invention and the aqueous solutions and above-mentioned mixtures thereof as low-foam wetting agents for emulsion polymerization.

The present invention also relates to aqueous polymer dispersions obtainable by emulsion polymerization using the substances according to the invention and aqueous solutions thereof as emulsifiers and/or wetting agents and/or auxiliaries for post-stabilization.

The present invention also relates to the use of the substances according to the invention and the aqueous solutions and above-mentioned mixtures thereof as additives in cosmetic and/or pharmaceutical compositions and in compositions suitable for nutrition (i.e. compositions for human and/or animal nutrition). In this case, the additive can perform different functions. In particular, it can act as a wetting agent, emulsifier or dispersant.

It has also surprisingly been found that paints can be produced with the substances according to the invention, more particularly the salts of di-2PH-sulfosuccinate, which show a considerably better resistance to water after drying than corresponding di-2EH-sulfosuccinate-based paints. Accordingly, the present invention also relates to the use of the substances according to the invention and the aqueous solutions and above-mentioned mixtures thereof as paint additives.

EXAMPLES

Substances Used

Di-(2-ethylhexyl)-maleate was obtained from Celanese, sodium disulfite and 2-propylheptanol from BASF, maleic anhydride from Sasol-Huntsman and NeoPac E-106 (PU acrylate dispersion) from DSM. Hydropalat 875 (anionic wetting agent), DSX 1514 (polyurethane prepolymer) and Dehydran 1293 (solution of a modified polydimethyl siloxane) are products of Cognis.

Production Examples

Example 1 (Comparison)

Production of Sodium di-(2-ethylhexyl)-sulfosuccinate (Solution in Water/Ethanol)

556 g (1.63 mol) di-(2-ethylhexyl)-maleate, 40 g Hydropalat 875, 160 g (0.84 mol) sodium disulfite and 194 g deionized water were introduced into a 1-liter four-necked flask equipped with a mechanical stirrer, heating system, reflux condenser and nitrogen inlet and were heated under reflux at 104° C. in a gentle stream of nitrogen until a clear solution was obtained (ca. 3 hours). After stirring for 10 minutes, no more sulfite could be detected in the product. On cooling, the product gelled/solidified which could be avoided by addition of a co-solvent: to this end, 50 g ethanol was added at ca. 80° C. The solution thus obtained contained 75% by weight sulfosuccinate and had the following characteristic data: Epton: 16.39%; dry residue: 74.29%.

Example 2 (Invention)

Production of di-(2-propylheptyl)-maleate 392 g (4.0 mol) maleic anhydride, 1330 g (8.4 mol) 2-propylheptanol and 8.6 g (0.05 mol) p-toluenesulfonic acid monohydrate were weighed under nitrogen into a 2-liter four-necked flask equipped with a mechanical stirrer, heating system, distillation column and nitrogen/vacuum connection and were slowly heated to 140° C. The water of reaction formed was removed by distillation. As soon as only a little distillate passed over (ca. 3.5 hours after the beginning of the reaction), the pressure was slowly reduced to 10 mbar and maintained for 3 hours. The product obtained had a residual acid value of 1.66 mg KOH/g.

Example 3 (Invention)

Production of Sodium di-(2-propylheptyl)-sulfosuccinate (Solution in Water/Ethanol)

574 g (1.45 mol) di-(2-propylheptyl)-maleate (produced in accordance with Example 2), 40 g of a solution of (a) 70% di-(2-propylheptyl)-sulfosuccinate, (b) 20% water and (c) 10% ethanol (note—the solution of the three components (a), (b) and (c) is obtained as the product of the described synthesis of Example 3. When Example 3 was carried out for the first time, the mixture of components (a), (b) and (c) was not yet available—40.0 g Hydropalat 875 were used instead), 142 g (0.75 mol) sodium disulfite and 194 g deionized water were introduced into a 1-liter four-necked flask equipped with a mechanical stirrer, heating system, reflux condenser and nitrogen inlet and were heated under reflux at 104° C. in a gentle stream of nitrogen until a clear solution was obtained (ca. 3 hours). After stirring for 10 minutes, no more sulfite could be detected in the product. On cooling, the product gelled/solidified which could be avoided by addition of a co-solvent: to this end, 50 g ethanol was added at ca. 80° C. The product thus obtained had the following characteristic data: acid value 0.18 mg KOH/g; Epton: 14.01%; dry residue: 71.66%; sodium sulfate content 0.32%.

Application Examples

Example 4

Measurement of Dynamic Surface Tension

The solutions obtained in accordance with Examples 1 and 3 were diluted with water to a concentration of 0.1% by weight each of di-2-ethylhexyl sulfosuccinate, Na salt (di-2-EH-SUS), and di-2-propylheptyl sulfosuccinate, Na salt (di-2-PH-SUS). The dynamic surface tension of these solutions was determined with a Krüss bubble tensiometer at various bubble frequencies The results can be found in Table 1.

TABLE 1

| Bubble frequency [Hz] | Dyn. surface tension [mN/m] | |
| --- | --- | --- |
| | Di-2-EH-SUS (comparison) | Di-2-PH-SUS (invention) |
| 0.1 | 33.8 | 26.1 |
| 0.5 | 36.1 | 26.9 |
| 1.0 | 37.2 | 28.3 |
| 5 | 39.5 | 41.5 |
| 10 | 40.6 | 50.9 |

Example 5

Water Resistance of Paints

Water stability was determined to DIN 68861. To this end, a basic paint was first produced as follows:

To produce 100 g of the basic paint, 40.0 g NeoPac E-106 and 0.3 g DSX 1514 were introduced first and, with the dissolver running, 2.2 g butyl glycol, 2.2 g methyl diglycol, 1.0 g Dehydran 1293, 53.6 g NeoPac E-106 and 0.7 g deionized water were added in that order.

The basic paint was then provided with 0.7% by weight of the sulfosuccinate solution to be tested and the formulation obtained was knife-coated onto a glass plate (layer thickness 150 μm). After drying for 7 days at 20° C., drops of water were applied and were left to act for 8 hours. The change in the paint surface was then evaluated to DIN 53230.

The results can be found in Table 2. The scale on which the water resistance data in Table 2 are based ranges from 0 to 5 (on the lines of a school marking system) where 0="no change" and 5="marked change".

TABLE 2

| Paint | Water resistance evaluated to DIN 53230 |
| --- | --- |
| Basic paint + 0.7% by weight di-2-EH-SUS solution (Example 1) | 3 |
| Basic paint + 0.7% by weight di-2-PH-SUS solution (Example 1) | 1 |

It can clearly be seen that the paint based on the Example according to the invention (i.e., di-2-PH-SUS) has a far better water resistance than the paint based on the Comparison Example (i.e., di-2-EH-SUS).

What is claimed is:

1. A compound consisting of a salt of a mono- and/or di-2-propylheptyl ester of a sulfonated dicarboxylic acid corresponding to formula (I):

$$R^1O_2C-CH_2-CH(SO_3M^1)-CO_2R^2 \qquad (I)$$

wherein $M^1$ is a cation, and $R^1$ and $R^2$ independently have the same meaning as $M^1$, or represent an alkyl group selected from the group consisting of n-$C_5H_{11}$CH($C_3H_7$)CH$_2$—, $C_2H_5$CH(CH$_3$)CH$_2$CH($C_3H_7$)CH$_2$—, and CH$_3$CH(CH$_3$)CH$_2$CH$_2$CH($C_3H_7$)CH$_2$—, wherein not more than one of the substituents $R^1$ and $R^2$ may be $M^1$.

2. The compound according to claim 1, wherein said 2-propylheptyl ester contains at least 98% of n-$C_5H_{11}$CH($C_3H_7$)CH$_2$— as the alkyl group.

3. The compound according to claim 1, wherein said 2-propylheptyl ester is an isomer mixture of:
a) 70 to 99% of n-$C_5H_{11}$CH($C_3H_7$)CH$_2$—; and
b) 1 to 30% of a mixture of $C_2H_5$CH(CH$_3$)CH$_2$CH($C_3H_7$)CH$_2$— and CH$_3$CH(CH$_3$)CH$_2$CH$_2$H($C_3H_7$)CH$_2$— as the alkyl group.

4. The compound according to claim 1, wherein $M^1$ is selected from the group consisting of sodium, potassium, and ammonium.

5. A composition consisting of:
(a) one or more compounds of claim 1;
(b) one or more organic solvents, liquid at 20° C., with a boiling point above 250° C. at 1 bar; and
(c) optionally, one or more short-chain alcohols and/or water.

6. The composition according to claim 5, wherein said one or more organic solvents are selected from the group consisting of nonionic surfactants.

7. The compound according to claim 1, incorporated into an emulsion as an emulsifier and/or dispersant for emulsion polymerization.

8. An emulsion comprising the compound of claim 1, wherein said emulsion is a low-foam wetting agent for emulsion polymerization.

9. A stabilizer for emulsion polymerization comprising the compound of claim 1, wherein said stabilizer stabilizes an aqueous polymer dispersion obtained by emulsion polymerization.

10. A paint comprising the compound of claim 1.

11. The composition according to claim 5, incorporated into a paint.

12. A cosmetic, pharmaceutical, or nutritional composition comprising the compound of claim 1.

13. The composition according to claim 5, incorporated into a cosmetic, pharmaceutical, or nutritional composition.

* * * * *